United States Patent [19]

Calderazzo et al.

[11] 4,006,174

[45] Feb. 1, 1977

[54] PROCESS FOR THE PREPARATION OF URANIUM (IV) CHELATED COMPOUNDS AND THORIUM CHELATED COMPOUNDS

[75] Inventors: Fausto Calderazzo, Ghezzano; Marco Pasquali, Pisa; Pierpaolo Garibaldi, San Donato Milanese, all of Italy

[73] Assignee: Snam Progetti S.p.A., Milan, Italy

[22] Filed: Oct. 25, 1974

[21] Appl. No.: 518,193

[52] U.S. Cl. ............................................ 260/429.1
[51] Int. Cl.² .......................................... C07F 5/00
[58] Field of Search ................................. 260/429.1

[56] References Cited

UNITED STATES PATENTS 3,198,817  8/1965  Langer ........................... 260/429.1

OTHER PUBLICATIONS

Jones et al., J. Am. Chem. Soc., vol. 78, pp. 4289–4290.
Martell et al., Chemistry of the Metal Chelates, Prentice–Hall, Inc., N.Y., 1952, pp. 324–325.
Carey et al., J. Am. Chem. Soc., vol. 90, pp. 32–38, (1968).

*Primary Examiner*—Leland A. Sebastian
*Attorney, Agent, or Firm*—Ralph M. Watson

[57] ABSTRACT

A chelated compound of uranium (IV) or thorium is prepared by reacting an anhydrous halide of uranium (IV) or thorium with a chelating agent such as acetylacetone in the presence of an anhydrous solvent and gaseous ammonia in the temperature range of 10 to 60° C.

3 Claims, No Drawings

PROCESS FOR THE PREPARATION OF URANIUM (IV) CHELATED COMPOUNDS AND THORIUM CHELATED COMPOUNDS

The present invention relates, in particular, to a process for the preparation of are uranium (IV) chelated compound starting from an uranium (IV) halide in the presence of gasous ammonia.

It is known that it is possible to synthetize uranium (IV) chelated compounds by treating chelating organic acids with aqueous solutions of uranium halides. However, the uranium halide, dissolved in water, may undergo hydrolisis reactions and give rise to soluble species containing the cation $UO^{2+}(aq)$.

We have now found a simple process for the synthesis of uranium (IV) chelated compounds starting from anhydrous uranium halides which are treated with the chelating agent in the presence of a solvent containing no water and gaseous ammonia.

The reaction occurs according to the following stoichiometry $$UX_4 + nBH + 4NH_3 \rightarrow 4NH_4X + UB_n$$

wherein X means the halide ion, BHx is the chelating agent selected from acetylacetone (AcacH), dibenzoylmethane (DBMH), dipivalylmethane (DPMH), N-methylsalicylidenemine (Me-SalH) or the quadridentante Schiff base N,N'-ethylenebis (salicylideneimine), n is an integer selected from 4 and 2, x is 2 in the case of the quadridentate base and to 1 in the other cases.

The reaction runs completely towards the formation of the final products and products other than the mentioned ones are not observed. It is carried out in the presence of an anhydrous solvent selected from tetrahydrofuran, ethers, acetone, at temperatures of from 10° to 60° C.

The uranium (IV) chelated compounds according to the present invention can be employed as catalysts in the polymerization reactions of conjugated dienes as such or mixed with suitable co-catalysts.

EXAMPLES 1–5

We detail only the preparation of USalen$_2$ since the other derivatives are prepared in the same way:

3.12 g (8.21 mmoles) of anhydrous uranium tetrachloride were dissolved into 100 ml of tetrahydrofuran and treated with 4.40 g of N,N'-ethylenebis salicilydeneimine (16.40 mmoles) also dissolved into 100 ml of tetrahydrofuran.

After the addition of Schiff base, gaseous ammonia was added to the reaction mixture which was kept under stirring till no more ammonia adsorption was observed. Finally the reaction mixture was filtered and separated from ammonium chloride which was repeatedly washed in order to dissolve possible traces of the uranium complex. The NH$_4$Cl amount was 98 % of theoretical. The filtered solution was partially evaporated under reduced pressure and the precipitation of the uranium complex was facilitated by adding heptane. 5.9 g were obtained at a yield of about 93%.

The table reports the data on the above complex and on other derivatives obtained in a similar way.

TABLE 1

Properties of uranium (IV) chelated compounds

| Compounds | Formula | | Molecular Weight | Colour | Magnetic moment eff. (BM) 10 × diamagnetic correction (cgsu) | Yield %[1] |
|---|---|---|---|---|---|---|
| U(Acac)$_4$ | (I) | $C_{20}H_{28}O_8U$ | 634.5 | Green | 2.67 | 60.0 |
| U(DBM)$_4$ | (II) | $C_{60}H_{44}O_8U$ | 1131.0 | Green | | 87.5 |
| U(DPM)$_4$ | (III) | $C_{44}H_{76}O_8U$ | 971.1 | Green | 2.81 | 58.5 |
| U(Me-Sal)$_4$ | (IV) | $C_{32}H_{32}N_4O_4U$ | 774.7 | Brown | | 63.2 |
| USalen$_2$ | (V) | $C_{32}N_{28}N_4O_4U$ | 770.6 | Brown | 2.66 | 92.7 |

[1]Yield as analytically pure product. At least three elements were analyzed for each compound.

EXAMPLE 6

Preparation of Th Salen$_2$

Anhydrous thorium tetrachloride (1.6 g; 4.28 mmoles) was suspended in 100 ml of anhydrous tetrahydrofuran and treated, at room temperature, with SalenH$_2$ (2.30 g; 8.57 mmoles). That caused the formation of a yellow precipitate. The reaction vessel was set free by means of the water pump and then gaseous ammonia was introduced. The atmospheric pressure was kept till a further gas absorption was noted. The reaction mixture was stirred at room temperature for about twenty hours. After the removal of ammonium chloride by filtration, the solvent was partially evaporated under reduced pressure and n-heptane was then added to the resulting suspension in order to complete the precipitation of the complex. This latter was recovered by filtration and dried under vacuum (2.30 g; 70.3% yield). The compound was light rose coloured.

| | C | H | N | Th |
|---|---|---|---|---|
| Calculated | 50.27 | 3.69 | 7.33 | 30.35 |
| Found | 50.60 | 4.59 | 7.33 | 30.00 |

EXAMPLE 7

Preparation of U [(CH$_3$O)$_2$ Salen]$_2$

Anhydrous uranium tetrachmoride (6.61 g, 17.40 mmoles) was dissolved in tetrahydrofuran (400 ml) and CH$_3$O – Salen H$_2$ (11.40 g; 34.7 mmoles) was added to the resulting solution. The reaction vessel was then set free by means of the water pump and gaseous ammonia was added.

The procedure of the preceding example was followed but, in this case, most of the uranium complex was undissolved at the end of the reaction.

After about 20 hours stirring, the reaction mixture was filtered. The separated solid, containing both the complex and ammonium chloride, was washed with air free water in order to dissolve ammonium chloride. The resulting uranium complex (11.6 g; 75.0% yield) was slightly impure. The resulting compound, as obtained from the filtration of the reaction mixture, was partially evaporated under reduced pressure and gave rise to g 2.2 (14.2% yield) of a brown coloured analytical grade product.

Analysis for $C_{24}H_{24}N_4O_4U$

|  | C | H | N | U |
|---|---|---|---|---|
| Calculated | 48.54 | 4.07 | 6.29 | 26.72 |
| Found | 48.40 | 3.80 | 6.36 | 26.60 |

What we claim is:

1. The process of preparing a chelated compound of a metal selected from the group consisting of uranium (IV) and thorium which consists in reacting an anhydrous halide of uranium (IV) or thorium with a chelating agent in the presence of an anhydrous solvent and gaseous ammonia in the temperature range of from 20° to 60° C.

2. The process of preparing a chelated compound of a metal selected from the group consisting of uranium (IV) and thorium as claimed in claim 1, wherein the solvent is a member of the group consisting of tetrohydrofuran, ethers and acetone.

3. The process of preparing a chelated compound of a metal selected from the group consisting of uranium (IV) and thorium as claimed in claim 1, wherein the chelating agent is a member of the group consisting of acetylacetone, dibenzoylmethane, dipivalylmethane, N-methylsalicylideneimine and N,N'-ethylenebis (salicylideneimine).

* * * * *

UNITED STATES PATENT AND TRADEMARK OFFICE
CERTIFICATE OF CORRECTION

PATENT NO. : 4,006,174
DATED : February 1, 1977
INVENTOR(S) : Fausto Calderazzo, Marco Pasquali and Pierpaolo Garibaldi It is certified that error appears in the above–identified patent and that said Letters Patent are hereby corrected as shown below:

Page 1, after line 21, insert the following lines:

--[30] Foreign Application Priority Data

October 26, 1973   Italy............30597/73--.

Column 1, line 35, Correct "nBH" to read --$nBH_x$--.

line 40, Correct spelling of "methylsalicylideneimine".

line 62, Enclose "salicilydeneimine" in parenthesis --( )--.

Signed and Sealed this

Twenty-first Day of June 1977

[SEAL]

Attest:

RUTH C. MASON
*Attesting Officer*

C. MARSHALL DANN
*Commissioner of Patents and Trademarks*